(12) United States Patent
Model et al.

(10) Patent No.: US 8,482,733 B2
(45) Date of Patent: Jul. 9, 2013

(54) MEASUREMENT OF THE ABSORPTION COEFFICIENT OF LIGHT ABSORBING LIQUIDS AND THEIR USE FOR QUANTITATIVE IMAGING OF SURFACE TOPOGRAPHY

(75) Inventors: Michael A. Model, Chagrin Falls, OH (US); Anatoly K. Khitrin, Kent, OH (US)

(73) Assignee: Kent State University, Kent, OH (US)

( * ) Notice: Subject to any disclaimer, the term of this patent is extended or adjusted under 35 U.S.C. 154(b) by 280 days.

(21) Appl. No.: 12/172,666

(22) Filed: Jul. 14, 2008

(65) Prior Publication Data
US 2009/0027676 A1  Jan. 29, 2009

Related U.S. Application Data

(60) Provisional application No. 60/951,501, filed on Jul. 24, 2007.

(51) Int. Cl.
*G01N 21/00* (2006.01)
(52) U.S. Cl.
USPC ............................ 356/436; 250/428; 250/564
(58) Field of Classification Search
USPC ...................... 356/436; 250/428, 564, 559.27
See application file for complete search history.

(56) References Cited

U.S. PATENT DOCUMENTS

| 5,126,569 | A | * | 6/1992 | Carlson | 250/341.4 |
| 5,371,368 | A | * | 12/1994 | Alfano et al. | 250/341.1 |
| 5,428,447 | A | * | 6/1995 | Toida | 356/601 |
| 5,784,152 | A | * | 7/1998 | Heffelfinger et al. | 356/73 |
| 6,731,380 | B2 | * | 5/2004 | Amara et al. | 356/73 |
| 2003/0016362 | A1 | * | 1/2003 | Haswell et al. | 356/436 |
| 2004/0233452 | A1 | * | 11/2004 | Prelewitz | 356/436 |

OTHER PUBLICATIONS

J.A.E. Spaan, L.J. Garred and P. Van De Borne, Use of a Wedge Cuvette in Thin Layer Photometry and Its Application to Oximetry, Pflugers Archiv European Journal of Physiology, pp. 279-283.
L.I. Al'Peroich, Use of Layers of Uneven Thickness for Measuring Optical Constants of Liquids in the Region of Strong Absorption, Nov. 13, 1962, pp. 181-184.

* cited by examiner

*Primary Examiner* — Tarifur Chowdhury
*Assistant Examiner* — Isiaka Akanbi
(74) *Attorney, Agent, or Firm* — Han Loeser + Parks LLP; Scott M. Oldham, Esq.

(57) ABSTRACT

An optical measurement system for obtaining information such as the absorption coefficient of a light-absorbing liquid, or a surface profile of an object immersed in a light-absorbing liquid having a known absorption coefficient. The system includes a light source that transmits light through the liquid, a detector that records an image of the light transmitted through the sample and a processor or other means adapted to analyze the intensity distribution found on the image to generate information about the sample.

21 Claims, 5 Drawing Sheets

FIG-7

MEASUREMENT OF THE ABSORPTION COEFFICIENT OF LIGHT ABSORBING LIQUIDS AND THEIR USE FOR QUANTITATIVE IMAGING OF SURFACE TOPOGRAPHY

RELATED APPLICATION

This application claims benefit of U.S. Provisional patent application No. 60/951,501, filed on Jul. 24, 2007.

TECHNICAL FIELD OF THE INVENTION

In general, the present invention relates to an optical method of making measurements and related apparatus. In particular, the present invention relates to a system that records light intensity as it passes through a light-absorbing liquid positioned between two surfaces, generates an image that shows the measured variations in the light intensity, and extrapolates information about the liquid or the surfaces from the image.

SUMMARY OF THE INVENTION

The present invention generally provides an optical measurement method for obtaining information about a sample. The method includes placing a light-absorbing liquid between a first surface and a second surface, transmitting light through the liquid, detecting the intensity distribution of the light transmitted through the liquid, and deriving information about one or more of the surfaces or the liquid from the intensity distribution. The method may include the step of determining the absorption coefficient of the liquid. Once the absorption coefficient is known, a profile of a surface in contact with the liquid may be obtained by measuring the depth of the liquid between the first and second surfaces by the imaging method.

The present invention further provides an optical measurement method for obtaining information from a sample, the sample including a first surface and a second surface at least partially separated by a light-absorbing liquid having a known absorption coefficient. The method includes mounting the sample on a microscope, directing light from a source toward the sample, isolating a selected wavelength(s) of light transmitted through the liquid, detecting the intensity of light of the selected wavelength(s) with a detector, and analyzing an intensity distribution from said detector to determine a distance between the first surface and the second surface.

The present invention further provides an optical measurement system for analyzing a sample, the sample including a first surface and a second surface, wherein said first surface and said second surface are at least partially separated by a liquid having a known absorption coefficient. The system includes a light source adapted to direct light toward said sample, a detector adapted to record the light transmitted through said sample, means for analyzing the intensity distribution within said light transmitted through said sample, means for numerically fitting an equation to said intensity distribution to generate a profile of said second surface.

DETAILED DESCRIPTION OF THE INVENTION

Absorption spectrophotometry is used to measure the absorption coefficient ($\alpha$) and its wavelength dependence (spectrum), and is used in chemistry to characterize chemical compositions and measure concentration. Commercial photometers directly measure attenuation of light intensity, and are reliable to no more than about 10,000-fold attenuation. To analyze liquids with higher optical densities, these liquids are diluted to allow the use of the spectrophotometer by relying on the Bouger-Lambert-Beer law, which states that $\alpha$ is proportional to the concentration of the absorbing substance. The linear relationship predicted by this law does not always hold true, and deviations from it may indicate the formation of molecular aggregates within the substance that are of interest to a chemist. Consequently, for many applications, it is desirable to measure samples without dilution. Alternative methods exist, such as ellipsometry, attenuated total internal reflection, or acoustic spectroscopy, but these methods require great expertise and often the use of non-standard equipment.

Figure 1:
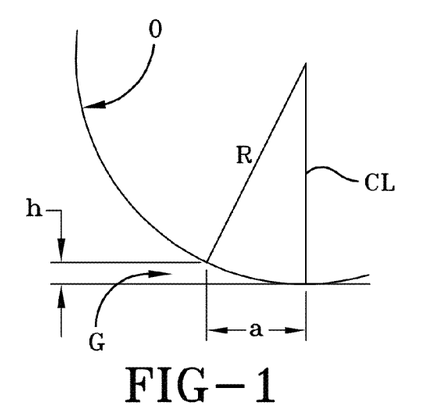
FIG. 1 is a schematic representation of a spherical surface resting on a flat surface depicting the gap formed between the spherical surface and the flat surface as a function of the distance from the contact point or centerline of the spherical surface.

In contrast, according to the present invention, the absorption coefficient (α) for a given liquid is obtained by measuring light intensity as it passes through a thin layer of liquid sandwiched between two transparent surfaces. For example, a spherical surface may be used as described below. As demonstrated schematically in FIG. 1, when considering a surface that is spherical near the point where it contacts a plane, the depth of the liquid (h) varies over a distance a from a contact line or centerline CL of the object O as a function of the distance a and the radius R of the spherical surface. For a spherical surface having a radius R of 0.5 centimeters, the depth or height h stays below 1 micrometer for up to a 100 micrometer distance a from the centerline CL. This area is large enough to be imaged with sufficient detail. When this gap G is filled with a liquid which needs to be analyzed, then a transmission image provides information about the liquid's absorption coefficient. For example, the absorption coefficient α can be calculated from a plot of transmitted intensity I, $$\ln I = \ln I_0 \alpha h \quad \text{(equation 1)}$$

where $I_0$ is the intensity at the contact point of the sphere and the flat surface, and h is the distance between the first surface and the second surface.

Figures 3A, 3B:
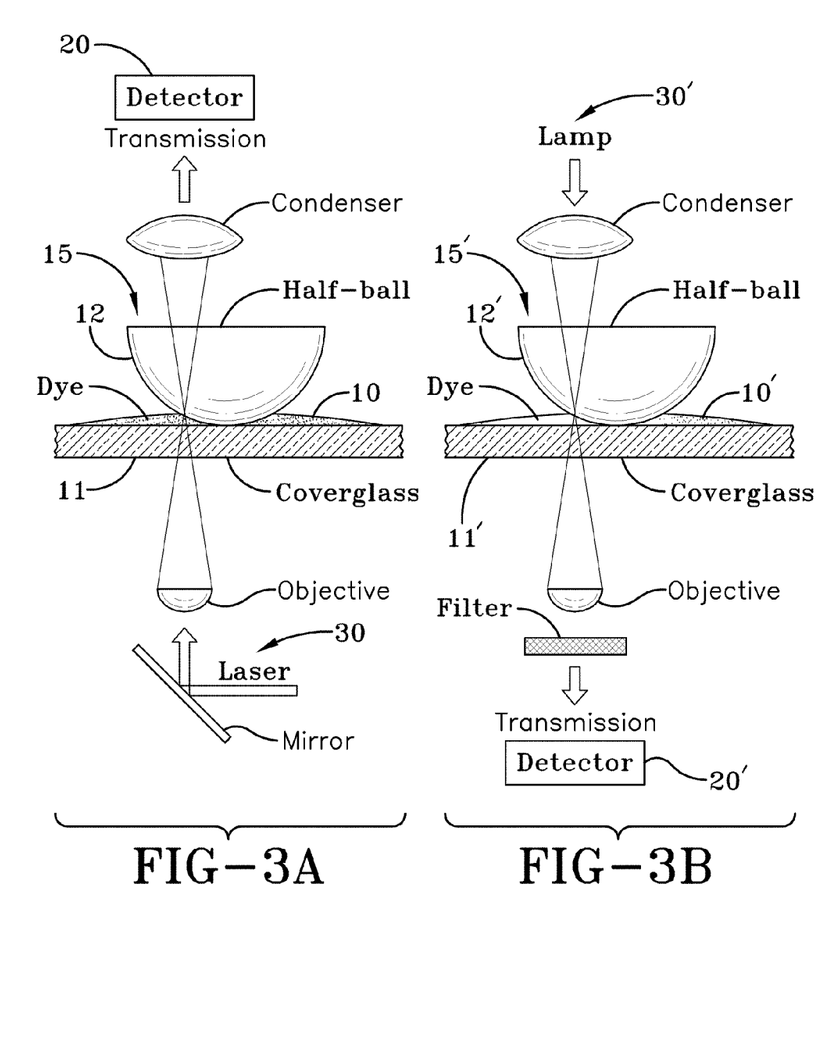
FIG. 3A depicts one system according to the concepts of the present invention employing an inverted laser scanning (confocal) microscope, where a small volume of dye has been placed on a flat slide and a curved object has been immersed in the liquid, where light from a source is transmitted through an objective and the light transmitted through the dye and curved object are collected by a condenser located above the curved object and where the light source is a laser providing scanning illumination of the sample.
FIG. 3B depicts an alternative system according to the concepts of the present invention where the light source is located above the condenser and a filter is located below the objective and where the light source is a lamp to obtain wide-field illumination of the sample.

As shown in FIGS. 3A and 3B, in accordance with the concepts of the present invention, a thin layer of light absorbing liquid 10, such as, for example, a dye (as shown), is placed on a flat transparent first surface 11, for example, a glass slide, and a second surface 12, for example, a half-ball lens 12, is placed in contact with the liquid 10 on the first surface 11. The lens 12 is mounted on a laser scanning (FIG. 3A) or a wide field (FIG. 3B) microscope for imaging.

The laser scanning arrangement (FIG. 3A) shows a small volume of light absorbing liquid 10 between a first surface 11, for example a slide, and a second surface 12, for example a half-ball lens. In this arrangement, light from a laser 30, is transmitted through an objective and focused at the interface between the dye and the lens. The light transmitted through the lens passes through a condenser and a image distribution is obtained by a detector 20.

The wide field arrangement (FIG. 3B) uses similar components; therefore, like numbers have been used to refer to the components in FIG. 3B and set off with a prime symbol for purposes of discussion. In the wide field arrangement, light source 30' is a lamp. Light from light source 30' is directed through the sample 15' before passing through the objective of the microscope. A filter may be located upstream of the detector 20' to filter the light transmitted from sample 15'. A condenser is located between the light source 30' and sample 15' to focus the light emitted from light source 30'.

In both arrangements, light is transmitted through the liquid layer, which has a variable thickness due to the presence of a surface, resulting in a transmitted image, which may De recorded by a detector 20. The image may be recorded in any suitable manner such as by a photomultiplier tube, a CCD camera, or similar detector 20 (FIGS. 3A and 3B).

Figure 4:
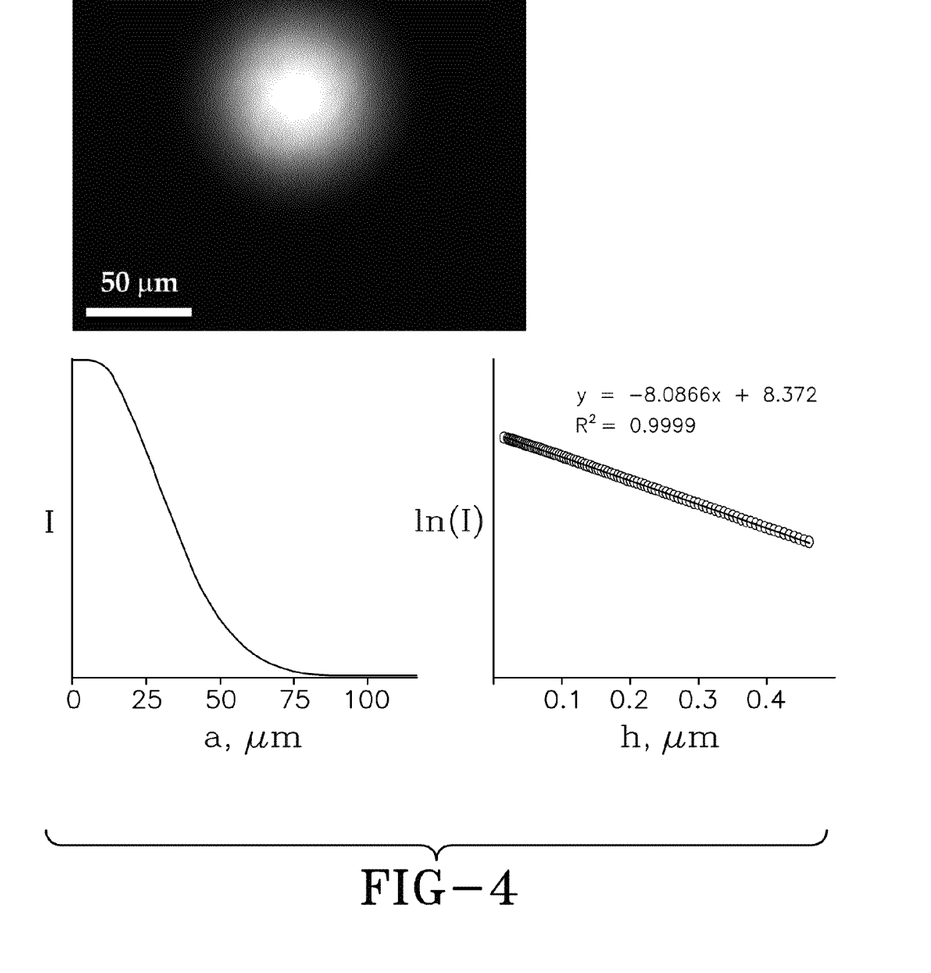
FIG. 4 depicts an image recorded by the system shown in FIG. 3A and corresponding radial profile plot.
Figure 5:
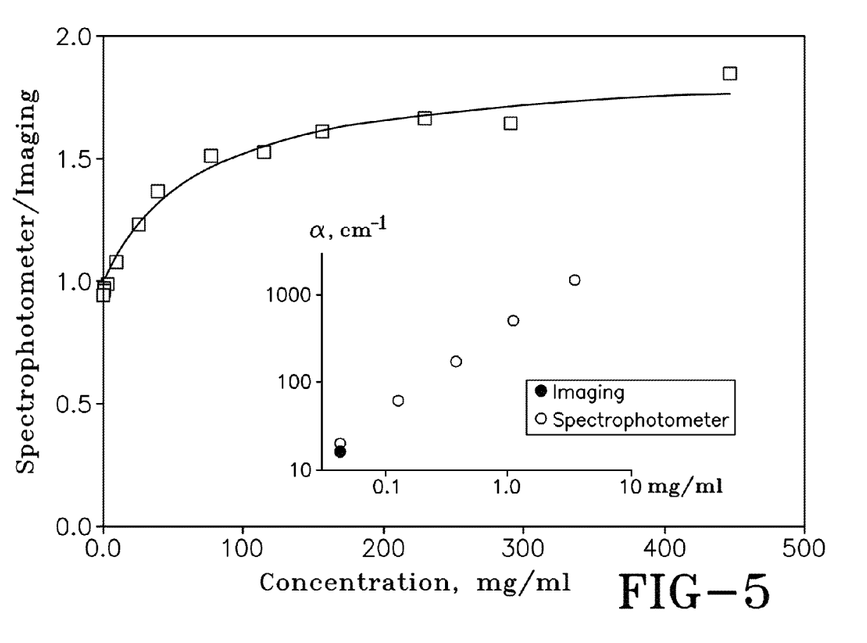
FIG. 5 is a plot comparing data obtained by the image-based method according to the concepts of the present invention and a spectrometry method, where the vertical axis shows the ratio of absorption coefficients of sodium fluorescein (NaFl) solutions obtained with the two methods. The samples were diluted for the spectrophotometric measurements. The insert shows the data for low concentrations in more detail.

As shown in FIG. 4, using the image obtained from the arrangements depicted in FIGS. 3A and 3B, the center of symmetry may be identified and a radial intensity distribution obtained. The radial coordinate is converted into depth according to:

$$h = r - \sqrt{r^2 - a^2} \approx a^2/2r$$

The intensity is converted into a logarithm. Then, the logarithm of intensity ln I is plotted against depth h, and a straight line is fitted through the points on the graph ln I=ln I(h). The slope of the best fit line provides the absorption coefficient α for the sample liquid.

Figure 3C:
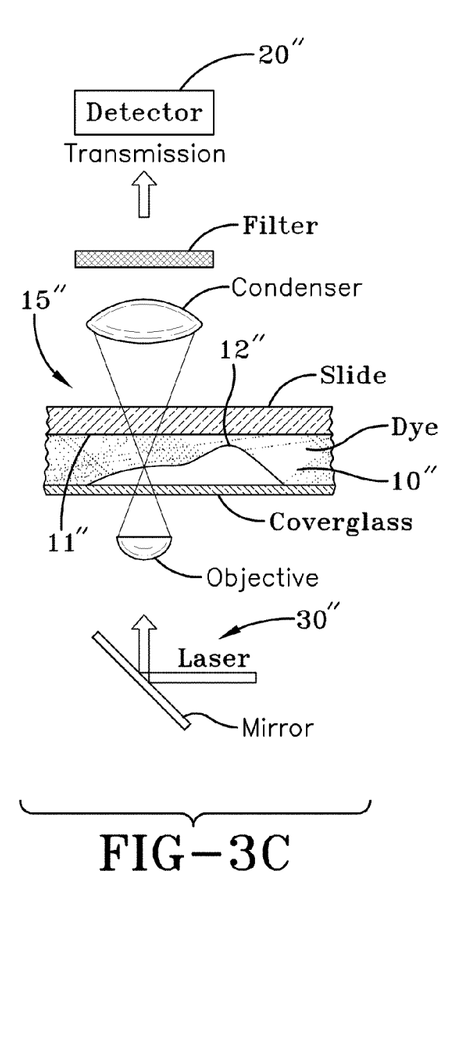
FIG. 3C depicts a system similar to the one depicted in FIG. 3A where biological cells and a slide are separated by a dye; the objective of the system is focused on the interface between the dye and the biological cells.

To perform qualitative imaging of surface topography, such as measuring a surface profile, the same apparatus used to obtain the absorption coefficient of a light absorbing liquid (FIGS. 3A and 3B) may be used. To ensure high resolution imaging, a coverglass may be used in place of a slide (FIG. 3).

If only one surface is being considered, to reduce the influence of the other surface, it is desirable to use a high quality surface so that any roughness or other imperfections may be ascribed to the measured surface. To that end, so called "super smooth" surfaces may be used. Alternatively, the non-measured surface may be treated to improve its quality. For example, when using a glass surface, suitable results were obtained by washing the glass with acids. It will be appreciated, however, in some cases, no treatment will be necessary.

In this technique, the absorption coefficient must be obtained or a liquid having a known absorption coefficient used. A logarithm is applied to the transmission image and divided by the absorption coefficient. The resulting intensity values provide the depth at every point of the image. For simplicity, this technique will be referred to as surface imaging or depth encoded contrast imaging.

Figure 2:
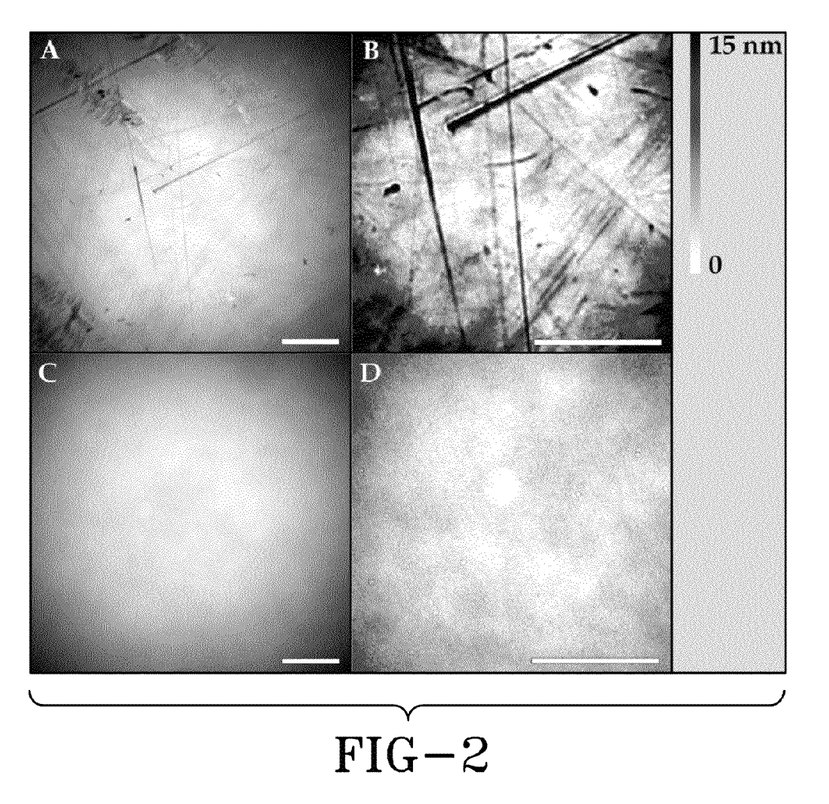
FIG. 2 depicts images of a lens with scratches (top) and a lens with a smooth surface (bottom) obtained using a system according to the concepts of the present invention, where the right side images depict depth profiles obtained from raw images shown on the left side by application of a logarithmic transformation, where the depth range is color coded according to the bar shown at the right of the Figure, the range depicted is 15 nanometers.

Imperfections in the measured surface may be visually apparent from the transmission image (FIG. 2). The top images in FIG. 2 show an old lens with numerous scratches. The bottom images show a new lens. A logarithmic unction:

$$D(x,y) = \frac{\ln I(x, y)}{\alpha'} \quad \text{(equation 2)}$$

was applied to the raw images on the left to convert the detected intensities into height values. In Equation 2, α' is the apparent absorption coefficient obtained with the particular high-NA lens that was used to obtain the image. A microscope objective or lens having a high numerical aperture (NA) may be used for surface measurements since the high-NA objective ensures a higher lateral resolution. The high-NA objective may require an additional calibration step. Calibration may be performed by determining the effective absorption coefficient α' as obtained with the high-NA objective. The α' value is expected to be slightly larger than true α because the rays travel, on average, a longer distance at more oblique angles. The effective α' would then be used for calculating surface profiles. The images appearing to the right of the raw images in FIG. 2 depict the height variation by color coding according to the bar at the far right of the figure.

The depth encoded contrast image may be corrected with respect to the reference level, for example, the brightest central spot for a lens placed on a cover glass. Further processing may be used to generate additional information from the depth-encoded contrast image. For example, the volume of an object may be obtained by integrating equation 2.

The surface imaging technique described above may also be applied to biological cells. The apparatus used in connection with the cell measurements (FIG. 3C) is similar in arrangement to the one depicted in FIG. 3A, and therefore, like numerals set off with a double prime (") will be used to refer to similar components. The optical measurement system includes an optional filter between the detector 20" and condenser. In the example shown, the cells were grown on a coverglass and immersed in a cell growth medium to which a dye 10" was added. The sample was mounted on a slide 11".

For quantitative measurements, the cells should be unaffected by the dye presence in the medium and remain impermeable to the dye.

When imaging adhered cells, there may be gaps filled with liquid between the base cell membrane and the substrate. In this case, the local intensity will indicate the overall cell thickness (rather than surface profile), and the integrated intensity will correctly represent the cell volume. To obtain details of a given surface of a cell, the objective is focused on that surface so that it appears sharp while the opposite surface will appear only as a slowly varying background to the image.

Further details of the present invention will become more apparent through the following examples.

EXAMPLES

Example 1

Liquid Property Measurements

The following description is one example of an embodiment according to the concepts of the present invention describing one possible system for determining properties of a liquid, such as the absorption coefficient of a liquid. This example is not to be considered limiting.

A light absorbing liquid was poured onto a flat surface in the form of a thick regular microscopy slide and a half-ball lens having a diameter of 10 millimeters ±4 micrometers and a surface quality 40-20 was immersed in the liquid. In a scanning laser confocal arrangement (FIG. 3A), light from a laser was delivered through a lens having a low numerical aperture value and focused on the top of the microscopy slide. Transmission images were recorded with respective detectors. In the example shown, the detectors were photomultiplier tubes.

In a wide-field configuration (FIG. 3B), white light from a tungsten-halogen lamp was focused on the sample by a condenser. On the opposite side of the sample, a band-pass filter was placed to select the spectral region around the peak of the dye absorbance. The image was recorded with a SensiCam QE CCD digital camera. A radial intensity distribution was analyzed with ImageJ software. Numerical fitting of the transmitted intensity distribution to equation 1 was done with spreadsheet software, namely, Excel software.

To provide a well-defined pathlength through the liquid, an objective with a low numerical aperture value (NA) was used. For example, an objective with NA 0.4 limits the half-angle of the light cone to 23.6 degrees. When light enters water, the angle is further reduced to 17.7 degrees. This results in only a 5 percent longer path for the marginal rays compared to the central rays. The actual difference is still less because the objective in the scanning confocal microscope (FIG. 3A) is illuminated by a truncated Gaussian beam so that contribution of the peripheral rays is less than in a uniform illumination. Objectives 4/0.16 or 20/0.7 also were found suitable for determining the absorption coefficient of the light absorbing liquid. It is believed that this method will tolerate imprecise focusing of the objective on the sample.

A sample made from a 50 percent weight to volume solution of acid fuchsin in water was placed between a slide and a hemi-spherical lens as described above. An image recorded from that experiment appears in FIG. 4. From FIG. 4, an absorption coefficient $\alpha$ was calculated to be 8.1 $\mu m^{-1}$ using scanned transmission image with a 543 nanometer laser line (FIG. 4). In this experiment $R^2$ was greater than 0.9999.

Figure 6:
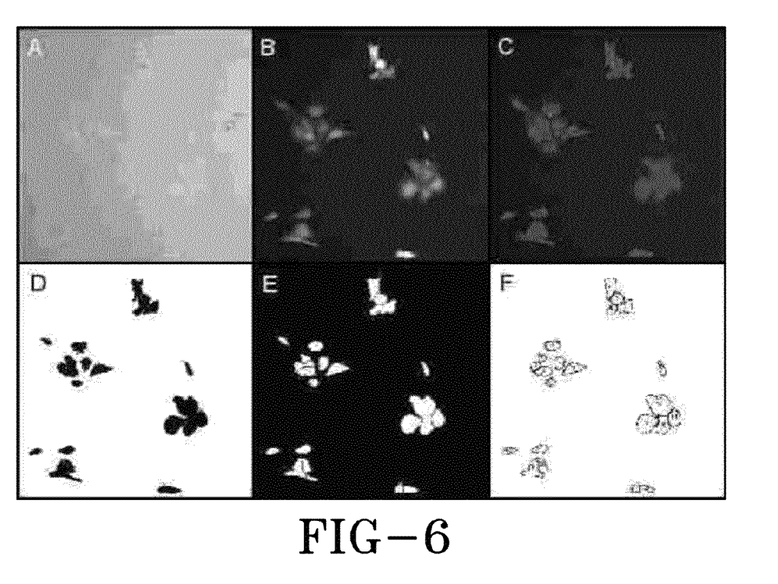
FIGS. 6A-F depict images recorded by a system according to the concepts of the present invention of a sample containing biological cells.

To compare these results with spectrophotometry, absorption of sodium fluorescein (NaFl) solutions were measured against the transmission-based method. The spectrophotometry samples were diluted in 10 mM Tris-HCl, pH 8.1, which is similar to a pH of concentrated NaFl in water, to obtain the optical density $A=\log(I_0/1) \approx 1$. At relatively low concentrations, the numbers obtained with both methods were similar as shown in FIG. 6. At high concentrations, overestimation of the absorption coefficient was observed with spectrophotometry. Measurements were obtained using an objective lens having an NA of 0.4.

Overall, based on the experiments, reliable and reproducible measurements for a wide range of absorption coefficients ($\alpha$), for example, from about 0.002 micrometer$^{-1}$ to over 10 micrometer$^{-1}$ are believed possible. Moreover, the lower limit could be extended by improving the homogeneity of the illumination. The upper limit has not been reached and the one found through experimentation is believed to be imposed by the solubility of the dye. In general, the upper limit can be extended by using surfaces of the highest possible quality.

Example 2

Surface Measurement

In a second example, surface characteristics of an object immersed in a light absorbing liquid or dye were determined using the method of the present invention. The following applications are provided as examples of the present invention, and should not be considered limiting.

Using a dye having a known absorption coefficient $\alpha$, the above-described methods were used to determine information about the surfaces between which the dye rested. With a dye solution having a very strong known absorption, up to about 12 micrometer$^{-1}$, attenuation of light provides very precise information about the depth of the dye layer. For example, this method could be used to test the quality of an optical lens (FIG. 2).

To produce the images shown in FIG. 2, a lens was placed on top of a flat high-quality surface and immersed in a liquid with a high and already known absorption coefficient 9.75 $\mu m^{-1}$. A detector collected the transmitted light and generated an image (FIG. 2). Contrast in the image reflects differences in the optical path through the liquid that is the distance between the first and second surfaces. Since the first (bottom) surface was flat and smooth, small-scale intensity variations in the image intensity reflect roughness of the surface of the lens. A logarithmic operation was then used to read the surface profile directly from the image (FIG. 2).

To generate the depth encoded images appearing on the right side of FIG. 2, ImageJ software was used to convert the recorded image into a 32-bit format to enable logarithmic processing according to Equation 2.

To improve lateral resolution, attention was paid to the glass thickness on which the liquid and lens rest. Since the microscope objective was designed for imaging through a 0.17 millimeter thick cover glass, a no. 1.5 cover glass (with nominal thickness 0.17 mm) was used to support the liquid and lens.

The resulting lateral resolution in this imaging method is determined by the numerical aperture (NA) of the objective and can be a fraction of a micron. The depth resolution can be on the order of a nanometer or less. If the intensity is related to the distance as $$I=I_0 e^{-ah}$$

then the error in the depth measurement is $$\Delta h = \frac{1}{\alpha} \frac{\Delta I}{I}$$

In the microscope used in the above example, $\Delta I/I$ was on the order of 0.003-0.01. Thus, if a dye has an absorption $\alpha=10$ $\mu m^{-1}$ then the expected error in the depth measurement can be below 1 nanometer.

FIG. 2 depicts examples of raw images on the left side, and images with intensity converted into a depth profile on the right side. The total depth range depicted in these images was 0-15 nm. Similar images were obtained with laser scanning and with wide-field illumination as described in the previous embodiments. Any dye with sufficiently strong absorption at available wavelength can be suitable for contrast generation.

A similar approach was applied to imaging of live biological cells as an additional example. In the example depicted in FIG. 6, quantitative measurements of the cells were made. For these measurements, the cells should be unaffected by the dye presence in the medium and remain impermeable to the dye. In the example shown, to impart contrast to the medium, the food colorant FD&C Blue 1 was used. FD&C Blue 1, when added to cell media at 5-10 mg/ml, does not penetrate the membranes of intact cells and shows no immediate toxicity. Visibility of cells in the bright field depends on cell structure and thickness, and FIG. 6A demonstrates that contrast in a bright-field image can be low. As demonstrated in FIG. 6B, adding dye to the medium makes the cells more visible by providing contrast. To perform cell counting as well as shape and volume analysis by computer, an intensity threshold may be applied (FIG. 6C). Then, the image may be converted to binary format (FIG. 6D). Watershed segmentation (FIG. 6E) was used to separate cells that are touching each other. Then the cells were thresholded again and counted (FIG. 6F). In this example, 22 out of 23 cells in the sample were counted. It can be seen that applying a light absorbing liquid, such as a dye, facilitates more accurate counting.

Figure 7:
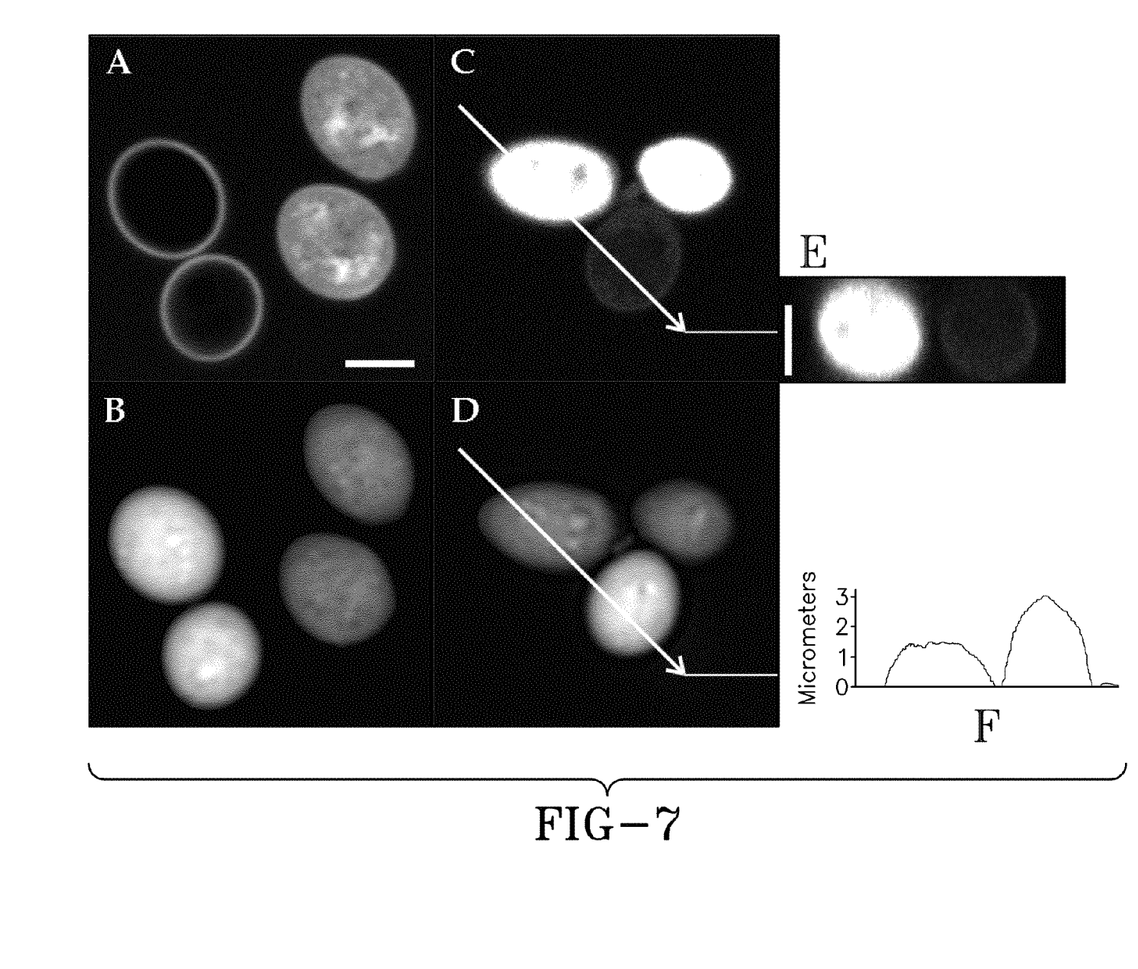
FIGS. 7A-D depict images of yeast cells obtained using the system of the present invention
FIG. 7E depicts a cross sectional view as might be seen along the line shown in FIG. 7C.
FIG. 7F depicts a surface profile obtained along the line depicted in FIG. 7D.

To obtain information about the surfaces of cells including shape and volume analysis, another example was considered and is discussed with reference to FIG. 7. In this example, chemically fixed baking yeast cells were used. The dry yeast was suspended in 9.5% sucrose and kept agitated for 2 hours. The cells were briefly exposed to either 25 µg/ml ethidium bromide or 25 µg/ml propodium iodide after which the dye was removed by triple centrifugation. These nucleic acid stains penetrate the membranes of dead, but not intact cells, and are used to assess cell viability. Cells were next fixed in 2% glutaraldehyde and the presence of 8 mg/ml BSA for 3 hours and mounted on a slide in 40 mg/ml NaFl ($\alpha'=1.33$ micrometer$^{-1}$ for the ×100/1.3 objective) was used. Due to the relatively large cell thickness, the dye concentration was reduced, relative to imaging of a lens surface described above, to meet the dynamic range of the instrument. In FIGS. 7A and B, the cells were stained with ethidium bromide, and in FIGS. 7C and 7D, the cells were stained with propidium iodide. Depth encoded contrast images were acquired by laser scanning at 488 nm through a 100/1.3 fluorite objective. Since at 40 mg/ml NaFl is brightly fluorescent, an additional 485/10 filter was placed on the condenser side to minimize contribution of fluorescence to the transmitted signal. Fluorescence of ethidium bromide and propidium iodide was excited with a HeNe laser at 543 nm, and collected through a 560LP filter. To create the vertical intensity profile (FIG. 7E) along the diagonal line shown in FIG. 7C, a stack of confocal images was collected at a 0.2 µm z-step. FIG. 7F displays intensity values of the corresponding depth encoded contrast image sampled along the same line in FIG. 7D. As indicated by the scale, cell depths ranging between 0 and 3 micrometers were obtained. Overall, for intact cells, the imaging method produced a thickness similar to the values observed with confocal fluorescence microscopy.

Overall, the system according to the concepts of the present invention provides a new and useful method of determining liquid absorption for a liquid. When the liquid absorption coefficient is known, the method may also be used to determine surface characteristics of an object placed in the liquid. The embodiments and examples herein are not limiting as various equivalents and substitutions may be made within the spirit of the invention.

The invention claimed is:

1. An optical measurement method for obtaining information about a light absorbing liquid, the method comprising:
   providing a first surface and a second surface at least partially separated by the light absorbing liquid, wherein the second surface extends above the first surface,
   transmitting light through the liquid;
   detecting the intensity of the light transmitted from the liquid;
   generating an intensity distribution from the detected intensity of the light; and
   deriving information including at least the absorption coefficient, of the liquid from said intensity distribution.

2. The optical measurement method of claim 1, wherein said step of deriving information about the liquid includes determining the thickness of the liquid between at least a portion of said first and second surfaces.

3. The optical measurement method of claim 1, wherein said step of deriving information includes numerically fitting an equation to said intensity distribution to determine the absorption coefficient of the liquid.

4. The optical measurement method of claim 1, further comprising generating a profile of said second surface from the height of the liquid between said first surface and said second surface.

5. The optical measurement method of claim 1, wherein said step of deriving information from said intensity distribution includes creating an image from the intensity of light transmitted through the liquid and applying an intensity threshold to said image.

6. The optical measurement method of claim 5, further comprising the step of converting the image to binary format.

7. The optical measurement method of claim 5, further comprising the step of counting objects within said image.

8. The optical measurement method of claim 1, further comprising the step of isolating a selective wavelength of light transmitted through said liquid before the step of detecting the intensity.

9. The method of claim 1, wherein the optical density of the liquid is higher than is measurable using a spectrophotometer.

10. An optical measurement method for determining features of objects on a surface, comprising:
   providing a light absorbing liquid having a known absorption coefficient on a surface with at least one object, wherein the liquid extends from a
   first surface to a second surface extending above the first surface;
   mounting the sample on a microscope;
   directing light from a source toward the sample;
   detecting the intensity of light transmitted through the sample; and
   analyzing the intensity of the transmitted light to determine a distance between the first surface and the second surface and characteristics of the at least one object.

11. The optical measurement method of claim 10, wherein the step of analyzing is repeated to generate a profile of said second surface.

12. The optical measurement method of claim 10, wherein said step of directing light from a source includes delivering light from a laser through a lens of a microscope.

13. The optical measurement method of claim 12 wherein said lens of said microscope has a high numerical aperture.

14. The optical measurement method of claim 10, wherein the step of transmitting light from a source includes focusing the light with a condenser.

15. The optical measurement method of claim 10, further comprising the step of isolating a selected wavelength or range of wavelengths by placing a band-pass filter upstream of said detector.

16. The optical measurement method of claim 15, wherein said band-pass filter is tuned to select the spectral region around the peak of the absorption coefficient of said liquid.

17. The optical measurement method of claim 10, wherein said step of analyzing includes applying a logarithm to the detected intensity of light transmitted through said liquid and the absorption coefficient of the light absorbing liquid to determine the distance between the first and second surfaces.

18. The optical measurement method of claim 17, wherein said second surface is located on a nanoscale object, wherein the step of analyzing includes determining the volume of said object by determining the distance between the first and second surfaces.

19. The optical measurement of claim 18, wherein said object includes a biological cell on the first surface.

20. The method of claim 10, wherein the absorption coefficient of the liquid is from about 0.002 micrometer$^{-1}$ to over 10 micrometer$^{-1}$.

21. An optical measurement system for analyzing a biological sample, the sample including at least one biological cell, the system comprising:

disposing a liquid having a known absorption coefficient on the biological sample to extend from a first surface to a second surface on said biological cell, and providing a light source adapted to direct light toward said biological sample;

a detector adapted to record the light transmitted through said sample;

means for analyzing the intensity distribution of the light transmitted through said sample to determine information about the at least one biological cell.

* * * * *